United States Patent [19]
Huang et al.

[11] Patent Number: 5,126,023
[45] Date of Patent: Jun. 30, 1992

[54] END-COLUMN ELECTRICAL AND ELECTROCHEMICAL DETECTOR FOR CAPILLARY ZONE ELECTROPHORESIS

[75] Inventors: Xiaohua Huang, Mountain View; Richard N. Zare, Stanford, both of Calif.; Andrew G. Ewing; Sandra E. Sloss, both of State College, Pa.

[73] Assignee: The Board of Trustees of the Leland Stanford Junior University, Stanford, Calif.

[21] Appl. No.: 580,259

[22] Filed: Sep. 10, 1990

[51] Int. Cl.$^5$ ...................... B01D 57/02; B01D 61/42
[52] U.S. Cl. ............................... 204/180.1; 204/299 R
[58] Field of Search ........................ 204/299 R, 180.1

[56] References Cited

U.S. PATENT DOCUMENTS 4,909,919 3/1990 Morris et al.

OTHER PUBLICATIONS

Wallingford & Ewing, Capillary Zone Electrophoresis w/Electrochemical Detection, Anal. Chem. 59, 1762-1766, (1987).
Huang, Gordon & Zare, Quant. of Li+ in Serum by Capillary Zone electrophoresis with on–column conductivity detector, J. of Chrom., 425, 385-390 (1988).
Wallingford & Ewing, Amperometric Detection of Catechols in Capillary Zone Electrophoresis w/Normal & Micellar Solutions, Anal. Chem., 60, 258-263 (1988).
Mikkers et al., "High-Performance Zone Electrophoresis", J. Chromatogr., 169 (1979), 11-20.
Jorgenson et al., "Zone Electrophoresis in Open-Tubular Glass Capillaries", Anal. Chem., 53 (1981), 1298-1302.
Jorgenson et al., "Capillary Zone Electrophoresis", Science 222 (1983) 266-272.
Hjerten, "Electrophoresis: A Survey of Techniques and Applications", J. Chromatogr., 347 (1985), 191-198.
Hjerten, et al., "Carrier-Free Zone Electrophoresis, Displacement Electrophoresis and Isoelectric Focusing in a High-Performance Electrophoresis Apparatus", J. Chromatogr., 403 (1987), 47-61.
Huang et al., "On-Column Conductivity Detector for Capillary Zone Electrophoresis", Anal. Chem., 59 (1987), 2747-2749.
Gordon et al., "Capillary Electrophoresis", Science 242 (1988), 224-228.
Huang et al., "Quantitation of Li+ in Serum by Capillary Zone Electrophoresis with An On-Column Conductivity Detector", J. Chromatogr., 425 (1988), 385-390.
Wallingford et al., "Retention of Ionic and Non-Ionic Catechols in Capillary Zone Electrophoresis with Micellar Solutions", J. Chromatogr., 441 (1988), 299-309.
Smith et al., "Capillary Zone Electrophoresis-Mass Spectrometry Using an Electrospray Ionization Interface", Anal. Chem., 60 (1988), 436-441.
Wallingford et al., "Capillary Zone Electrophoresis with Electrochemical Detection in 12.7 μm Diameter Columns", Anal. Chem., 60 (1988), 1972-1975.
Kuhr et al., "Optimization of Sensitivity and Separation in Capillary Zone Electrophoresis with Indirect Fluorescence Detection", Anal. Chem., 60 (1988), 2642-2646.
Wallingford et al., "Separation of Serotonin form Catechols by Capillary Zone Electrophoresis with Electrochemical Detection," Anal. Chem., 61 (1989), 98-100.

(List continued on next page.)

Primary Examiner—John Niebling
Assistant Examiner—Caroline Koestner
Attorney, Agent, or Firm—Majestic, Parsons, Siebert & Hsue

[57] ABSTRACT

Electrical and electrochemical end-column detectors are provided in which the sensing microelectrode is placed at the outlet of the separation capillary. The novel design minimizes the electrical interference caused by the applied high voltage during CZE separations, and provides for detectors that are easy to construct, sensitive, reliable, and easy to operate.

19 Claims, 2 Drawing Sheets

OTHER PUBLICATIONS

Pentoney et al., "On-Line Radioisotope Detection for Capillary Electrophoresis", *Anal Chem.*, 61 (1989), 1642–1647.

Huang et al., "Analysis of Factors Causing Peak Broadening in Capillary Zone Electrophoresis", *J. Chromatogr.*, 480 (1989), 95–110.

Moseley et al., "Coupling of Capillary Zone Electrophoresis and Capillary Liquid Chromatography with Coaxial Continuous-Flow Fast Atom Bombardment Tandem Sector Mass Spectroscopy", *J. Chromatogr.*, 480 (1989), 197–210.

Caprioli et al., "Coupling Capillary Zone Electrophoresis and Continuous-Flow Fast Atom Bombardment Mass Spectroscopy for the Analysis of Peptide Mixtures", *J. Chromatogr.*, 480 (1989), 247–258.

Huang et al., "Effect of Electrolyte and Sample Concentration on the Relationship between Sensitivity and Resolution in Capillary Zone Electrophoresis using Conductivity Detection", *J. Chromatogr.*, 480 (1989), 285–288.

Huang et al., "Quantitative Analysis of Low Molecular Weight Carboxylic Acids by Capillary Zone Electrophoresis/Conductivity Detection", *Anal. Chem.*, 61 (1989), 766–770.

Ewing et al., "Capillary Electrophoresis", *Anal. Chem.* 61 (1989), 292A–303A.

Lee et al., "Liquid Junction Coupling for Capillary Zone Electrophoresis/Ion Spray Mass Spectrometry," *Biomed. Environ. Mass Spectrom.*, 18 (1989), 844–850.

Wallingford et al., "Capillary Electrophoresis" Chapter 1 in J. Giddings, Ed., *Advances in Chromatography* 29 (1989), 1–76, Marcel Dekker, Inc., New York.

Kuhr, "Capillary Electrophoresis", *Anal. Chem.*, 62 (1990), 403R–414 R.

END-COLUMN ELECTRICAL AND ELECTROCHEMICAL DETECTOR FOR CAPILLARY ZONE ELECTROPHORESIS

The government has rights in this invention, pursuant to NSF Contract No. CHE-8657193.

FIELD OF THE INVENTION

The invention relates generally to capillary electrokinetic devices and in particular to an improved system for detecting electrokinetically separated species with electrical or electrochemical measurement.

BACKGROUND OF THE INVENTION

Zone electrophoresis in capillaries has become an important technique in the repertoire of liquid-phase separations. See Jorgenson et al., Science 222 (1983) 266-272; Gordon et al., Science 242 (1988), 224-228; Ewing et al., Anal Chem. 61 (1989), 292A-303A; Wallingford et al., Advances in Chromatography 29 (1989), 1-76; and Kuhr, Anal. Chem., 62 (1990), 403R-414R. Capillary electrophoresis has been used for separations of small and large molecules and comprises several subtechniques including capillary zone electrophoresis (CZE), capillary gel electrophoresis, micellar electrokinetic capillary electrophoresis, and capillary isoelectric focusing. CZE employs extremely high potential fields, typically 300 V/cm, resulting in highly efficient separations of ionic solutes.

A major aspect of CZE in need of new development is detection; specifically, there is a critical need for detectors capable of responding to the small quantity of sample component in the effective detection volume. Detection schemes developed to date include direct and indirect UV absorption (Hjerten, J. Chromatogr., 347 (1985) 191-198 and Hjerten et al. J. Chromatogr., 403 (1987), 47-61), fluorescence (Jorgenson et al., Anal. Chem., 53 (1981), 1298-1302 and Kuhr et al., Anal. Chem., 60 (1988), 2642-2644)), and radioisotope (Pentoney et al., Anal. Chem., 61 (1989), 1642-1647) as well as mass spectrometric (Smith et al., Anal. Chem., 60 (1988), 436-441; Lee et al., Biomed. Environ. Mass Spectrom., 18 (1989), 844-850; Moseley et al., Chromatogr., 480 (1989), 197-210; Caprioli et al., J. Chromatogr., 480 (1989), 247-258)), and electrometric (Mikkers et al., J. Chromatogr., 169 (1979), 11-20; Huang et al., Anal. Chem., 59 (1987), 2747-2749; and Wallingford et al., Anal. Chem., 59 (1987), 1762-1766)) detectors.

Electrical detectors can be distinguished from electrochemical detectors. Electrochemical detectors involve electric effects due to chemical changes which occur when a particle or species enters the detection zone. Electrical detectors respond to changes in the conductance of current or changes of resistance which result when particles or species enter the detection zone. With electrical detectors no chemical reaction is necessarily associated or required. Existing electrical and electrochemical detectors for CZE use elaborate on-column and post-column detection schemes to prevent the high separation potentials used from interfering with the detection process. One scheme involves construction of 40-$\mu$m-diameter holes in the capillary using a laser. Thereafter, small platinum wire electrodes are placed in these holes to carry out on-column conductivity detection. It was demonstrated that the exact placement of these electrodes on opposite sides of the capillary is critical to minimize background noise associated with the high potential field used for separation. (Huang et al., Anal. Chem., 59 (1987), 2747-2749). In U.S. patent. application Ser. No. 443,059, filed Nov. 28, 1989, by Zare et al., on-column conductivity detectors were disclosed wherein on-column sensing electrodes are located contiguous with the exit of the separation microcolumn. The electrodes are covered on their side surfaces with electrical insulators so that conductivity is measured between their ends alone. Another scheme involves covering a crack in the capillary with a porous glass capillary (Wallingford et al., Anal. Chem., 59 (1987), 1762-1766)) to provide off-column amperometric detection.

Although good results have been obtained with current detection systems, they are unsatisfactory in that the structures involved are difficult to fabricate, expensive and, often times, unreliable. This has limited the routine application of both modes of electrochemical detection in CZE. See Ewing et al., Anal. Chem. 61 (1989), 292A-303A; Kuhr, Anal. Chem., 62 (1990), 403R-414R; Huang et al., Anal. Chem., 61 (1989), 766-770; Huang et al., J. Chromatogr., 425 (1988), 385-390; Huang et al., J. Chromatogr., 480 (1989), 285-288; Wallingford et al., Anal. Chem., 60 (1988), 1972-1975; Wallingford et al., Anal. Chem., 60 (1988), 258-263; Wallingford et al., J. Chromatogr., 441 (1988), 299-309; and Wallingford et al., Anal Chem., 61 (1989) 98-100.

SUMMARY OF THE INVENTION

It is an object of the present invention to provide reliable and relatively inexpensive off-column electrical and electrochemical detectors capable of responding to the small quantity of sample components in the effective detection volume in CZE.

It is another object of the present invention to provide end-column conductivity and amperometric detectors that eliminate detection problems associated with the high voltage drops across the capillary in CZE separations.

These and other objects are achieved by the present invention which provides a new design for CZE conductimetric and amperometric detectors in which a sensing microelectrode is placed at the outlet of the separation capillary. These "end-column detectors" are easy to construct. They do not suffer from electrical interference caused by the applied high voltage during the CZE separation. Moreover, end-column detectors demonstrate sensitivities approaching those of previous on-column conductivity and post-column amperometric detectors (Ewing et al., Anal. Chem. 61 (1989), 292A-303A; Huang et al., Anal. Chem., 59 (1987), 2747-2749; and Huang et al., Anal. Chem., 61 (1989), 766-770) with only a small sacrifice in resolution. Under typical operating conditions the use of an end-column CZE conductivity detector is found to cause extra zone broadening only about 25% larger than that associated with an on-column CZE conductivity detector. End-column amperometry provides detection limits as low as 56 amol with an efficiency of 143,000 theoretical plates for catechol.

DESCRIPTION OF A PREFERRED EMBODIMENT

Figure 1:
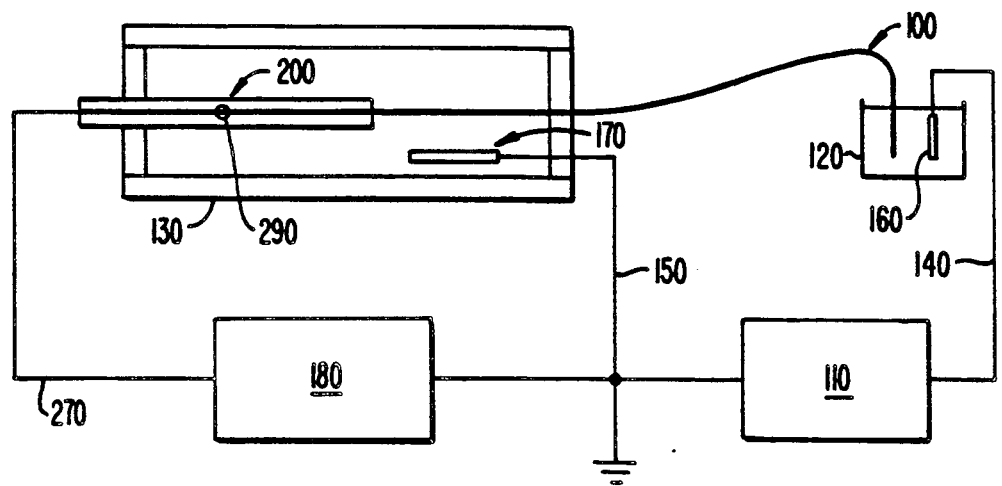
FIG. 1 is a schematic drawing of a CZE separation device with an end-column conductivity detector.

FIG. 1 shows a CZE separation device with an end-column conductivity detector. The separation capillary 100 is a 80 μm i.d., 354 o.d. fused silica microcolumn with a length of 60 cm (Polymicro Technologies, Phoenix, Ariz.). A reversible high voltage power supply 110 (Model R50B, Hipotronics, Inc., Brewster, N.Y.) provides a variable voltage of 0–30 kV with the outlet of the separation capillary at ground potential.

The capillary is liquid-filled with a support electrolyte and terminates near a sensing microelectrode inside plastic jacket 200. The jacket is approximately 25 mm long and has a diameter of approximately 6.4 mm. Inlet reservoir 120 and outlet reservoir 130 contain support electrolyte as well, so that the liquid-filled capillary 100 creates a continuous liquid and electrical connection between them. As will be further described below, the electrolyte exiting the capillary flows into the outlet reservoir by way of a hole 290 in the plastic jacket 200. The jacket is inserted part-way into the outlet reservoir through one of the reservoir walls and is held in position thereby. An effective electrokinetic voltage is supplied from power supply 110 through conductors 140 and 150 and grounding electrode 170 and electrode 160. A sensing microelectrode (described below) is situated at the outlet of the capillary 100 inside plastic jacket 200. The output of the end-column conductivity detector which varies as a function of the material in the electrolyte, is passed through lead 270 to conductivity meter 180, and is recorded. The conductivity measurement is made between the sensing microelectrode and the grounding electrode 170.

Figure 2:
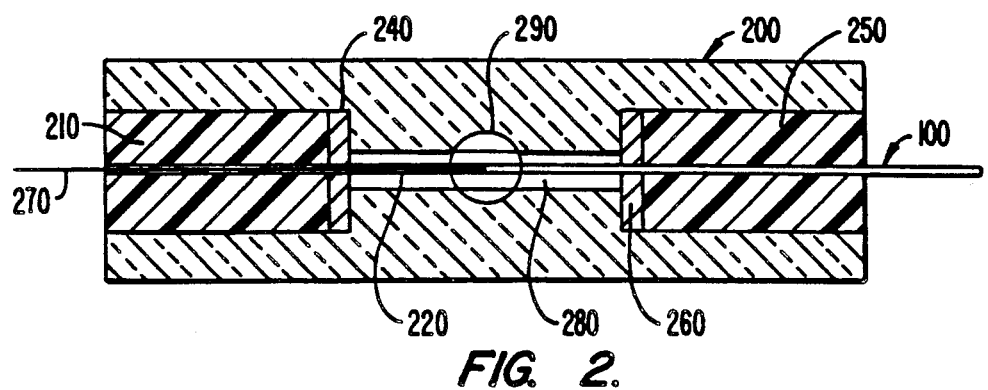
FIG. 2 is a cross-sectional view of the plastic jacket assembly.

FIG. 2 is a cross-sectional view of the plastic jacket assembly. Lead 270 is positioned inside the 1 cm long fused silica capillary 220 (150 μm i.d. and 355 μm o.d., Polymicro Technologies) that extends midway into the plastic jacket. Similarly, separation capillary 100 extends midway into the plastic jacket from the other direction. Epoxy 210 and Teflon ® washer 240 provide support for the capillary 220. Similarly, epoxy 250 and Teflon ® washer 260 provide support for separation capillary 100. Around its middle section, the plastic jacket defines channel 280 into which capillary 220 and separation capillary 100 are positioned. The channel is sealed at its ends by the Teflon ® washers 240 and 260. A hole 290 on one side of the plastic jacket lines up with the sensing microelectrode so that fluid flows off the separation capillary 100 and into the reservoir 130.

Figure 3:
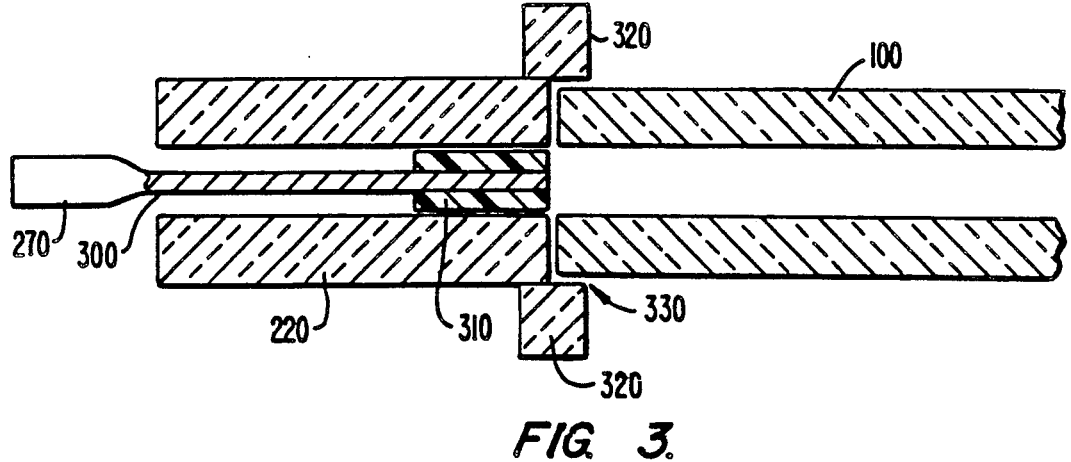
FIG. 3 is an enlarged view of the end-column sensing microelectrode.

FIG. 3 is an enlarged view of the sensing microelectrode 300, which is made of a 50 μm diameter platinum wire (California Fine Wire Co., Grover City, Calif.). The microelectrode is centered in capillary 220, and held in place by epoxy 310 (Torrseal, Varian Corp., Lexington, Mass.). The surface of the microelectrode facing the outlet of separation capillary 100 is sanded flat.

The end of capillary 220 facing the separation capillary is positioned inside a short but somewhat larger support fused silica capillary 320 (approximately 355 μm i.d.), which resembles a ring or collar structure. The outer surface at the end of capillary 220 is sealed with epoxy to the inner surface of one end of capillary 320. The other end of capillary 320 extends about 1-2 mm over the outlet end of the separation capillary 100, which is nearly butted against the sensing microelectrode 300. This leaves a small path or eluent gap 330, about 1-2 mm long, with a wall separation between separation capillary 100 and capillary 220 of approximately 1-5 μm, and preferably of approximately 1-2 μm, for the eluent to exit into the outlet reservoir 130 via hole 290. The eluent gap can be defined generally as a narrow channel that serves as the detection zone for electrical detectors. The dimensions of the eluent gap depend on, among other things, the amount of sample injected into the separation capillary for analysis. With the inventive conductivity detector, the resistance of each component zone or band is measured as each band flows through the eluent gap. If the gap length is too long, more than one band will be present in the eluent gap at a given time thereby interfering with the measurement. Increasing the wall separation distance reduces the gap length, but has the concomitant adverse effect of creating additional dead volume.

Figure 4:
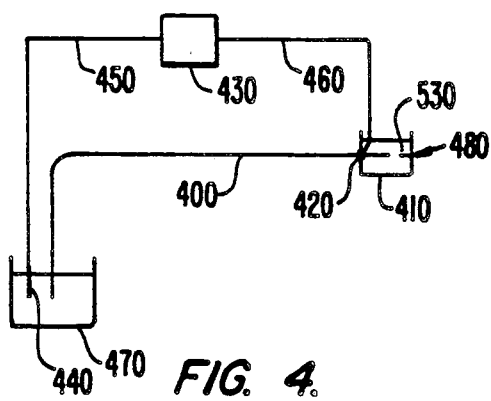
FIG. 4 is a schematic drawing of a CZE separation device with an end-column amperometric detector.

FIG. 4 is a schematic diagram of the CZE system used for amperometric measurements. The separation capillary 400 is a fused-silica capillary 5 μm i.d./140 μm o.d., Polymicro Technologies (Phoenix, Ariz.). The capillary (50–70 cm in length) is positioned in plastic vessel 410 through a bore defined by stainless steel fitting 420 (shown with size exaggerated) that is epoxied to one side of the vessel. The vessel functions as the electrochemical cell. The fitting also serves as the cathode for electrophoresis. The high voltage DC power supply 430 provides the electric field for electrophoresis. Electrode 440 situated in buffer reservoir 470 is connected to the power source by conductor 450. Similarly, stell fitting 420 is connected to the power source by conductor 460. The end of the microelectrode 530 (described below) of the detector 480 is manipulated through a slot cut into the opostie side of plastic vessel 410 and up against the end of the separtion capillary 400 with a micromanipulator (Newport, Model 422) while viewed under a microscope.

Figure 5:
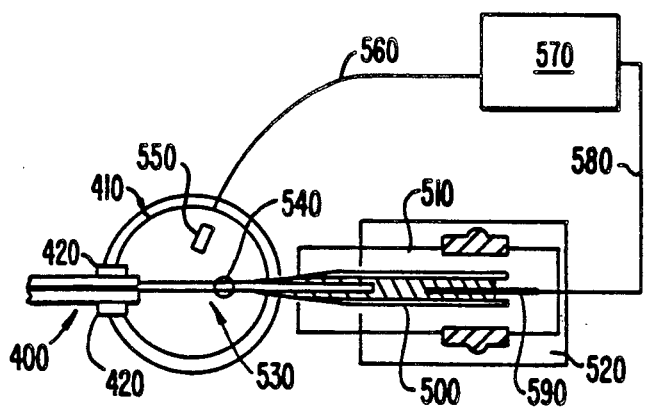
FIG. 5 is a schematic drawing of an end-column amperometric detector.

FIG. 5 is a schematic top view ofthe ampoteric detector. In constructing the detector, a single carbon fiber, 10 μm diameter, Amoco Performance Products, Greenville, S.C., is aspirated into glass capillary 500. The capillary was pulled around the fiber 530 with a vertical microelectrode puller. The fiber 530 serves as the microelectrode. Under an optical microscope, a drop of epoxy 540 is applied to the area where the fiber entered the glass capillary. After curing, the fiber is cut with a scalpel to an exposed length of 0.1-1 mm. The open end of the glas capillary is filled with mercury, a segment of nichrome wire 590 placed into it, and sealed with a drop of DUCO cement.

The carbon fiber detector is cemented onto a microscope slide 510 so that the end containing the exposed fiber protruded from the edge of the slide. The entire detector assembly is then placed onto a micromanipulator 520, Oriel Cor., Stratford, Conn. The tip of the carbon fiber is aligned with the bore of the separation capillary 400. The separation between the tip of the carbon fiber and the separation capillary is approximately 1-5 μm. The carbon fiber electrode 530 and outlet of the separation capillary 400 are submerged in the buffer solution of electrochemical cell 410 wherein a reference electrode 550 is also positioned. Reference electrode 550 is connected to potentiostat 570 by lead 560; nichrome wire 590 is connected to the potentiostat by lead 580.

EXPERIMENTAL

Conductivity Detection. For conductivity measurements, the end-column conductivity detector was placed directly at the outlet of the CZE capillary (as shown in FIG. 3). Samples were introduced by gravity at the cathodic or the anodic end of the capillary by raising the inlet a known height (7-12 cm) with respect to the outlet for a fixed period of time (5-10 s).

Amperometric Detection. For amperometric measurements, the cell was filled with 0.1M KCl as supporting electrolyte. Detection was performed in a 2-electrode configuration with a sodium saturated calomel reference electrode (SSCE). Electrochemical detection was carried out at 0.8 V SSCE. The low currents measured required that the detection end of the system be housed in a Faraday cage in order to minimize the effects of external noise sources. Injection was by electromigration Chemicals. All chemicals were from Sigma Chemical Corp. (St. Louis, Mo.) and were used without further purification. Conductivity detection runs were carried out with a buffer solution consisting of 20 mM morpholinoethanesulfonic acid (MES)/histidine at pH 6.0 to which a cationic surfactant, tetradecyltrimethylammonium bromide (TTAB), is added (1 mM final concentration). Water used to prepare solutions is freshly deionized and distilled with a water purifier (Model LD-2A coupled with a Mega-Pure Automatic Distiller, Corning Glassworks, N.Y.).

Amperometric detection runs were also carried out with MES, but these buffers were adjusted to the desired pH by addition of solid NaOH. Catecholamine stock solutions were prepared as 0.01 M solutions in 0.1M perchloric acid and diluted to the desired concentration with operating buffer.

RESULTS AND DISCUSSION

Figure 6:
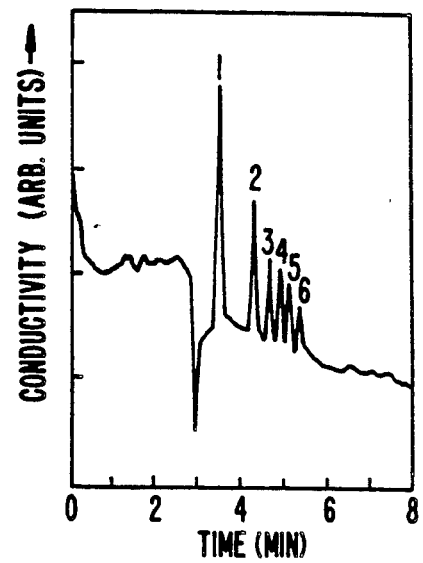
FIG. 6 is an electropherogram obtained with an end-column conductivity detector.

End-Column Conductivity Detection. FIG. 6 shows an electropherogram obtained when a mixture containing six different carboxylic acids at $5 \times 10^{-5}$M each is injected onto the CZE setup illustrated in FIGS. 1-3. The acids were: formate (peak 1), acetate (peak 2), propanoate (peak 3), butanoate (peak 4), pentanoate (peak 5), and hexanoate (peak 6). The CZE is operated at 20 kV and 8.8 μA. The buffer is MES/HIS (20 mM each) at pH 6 with 1 mM TTAB. Injection was by gravity.

The sensitivity and the resolution are quite similar to what has been observed previously (see FIG. 1 of Huang et al., *Anal. Chem.*, 61 (1989), 766-770). Because the TTAB in the buffer reverses the electroosmotic flow direction, the polarity of the power supply was also reversed so that the most mobile anion arrives first at the detector.

This end-column conductivity detector has more dead volume than an on-column conductivity detector. This additional dead volume estimated to be about 5-6 nL arises from the eluent gap 330 between capillaries 100, 220, and 320 as shown in FIG. 3. To investigate the effect of this dead volume on the separation efficiency, the following experiment was carried out. Benzoate anion ($C_6H_5COO^-$) was injected at $1 \times 10^{-5}$M and the peak profile was recorded using on-column UV absorption and end-column conductivity detection. The UV absorption detector was 9 cm upstream from the end-column conductivity detector, so that the additional zone broadening in traveling this distance is minimal (Huang et al., *J. Chromatogr.*, 480 (1984), 95-110). It was found that the peak from the end-column conductivity detector is 23% broader than that for the UV absorption detector, at an injection volume of 23 nL. This extra zone broadening caused by the additional dead volume of the end-column conductivity detector compares well with the estimated magnitude of the extra broadening.

For typical injection volumes (20 nL), and for a 80-μm-i.d. capillary, this extra zone broadening is less than 25%, which is modest compared to the advantage of such a simple construction. Moreover, the end-column conductivity detector can be readily fitted on the outlet of any capillary electrophoresis system, suggesting its use as a simple universal second detector for CZE separations. Furthermore, CZE employing the inventive conductivity detectors can yield quantitative measurements on an absolute basis when an internal standard is used.

End-Column Amperometric Detection. As described above, the CZE system for amperometric detection comprises essentially a fused-silica capillary and a carbon fiber microelectrode. With the inventive end-column amperometric detector, there is no need to isolate the sensing electrode from the high electric field needed for electrophoresis because the voltage drop outside the bore of the separation capillary is negligible. The microelectrode is aligned with the bore of the capillary and positioned up against but not into the capillary, thereby creating a thin layer cell at the capillary outlet. Because the diameter of the microelectrode in this embodiment is about twice the internal diameter of the capillary, good oxidation efficiency is obtained. Detector sensitivity is further increased by approximately one order of magnitude when a cylindrical carbon fiber electrode is used, as shown in FIG. 5, relative to a disk-shaped electrode. Apparently the eluent from the capillary forms a sheath-like flow around the electrode, providing more efficient oxidation of solutes at the detector. The separation conditions for the electropherograms in FIGS. 7 and 8 were: separation potential, 20 kV; electrochemical detector potential, 0.7 V; injection, 20 kV for 5 s.

Figure 7:
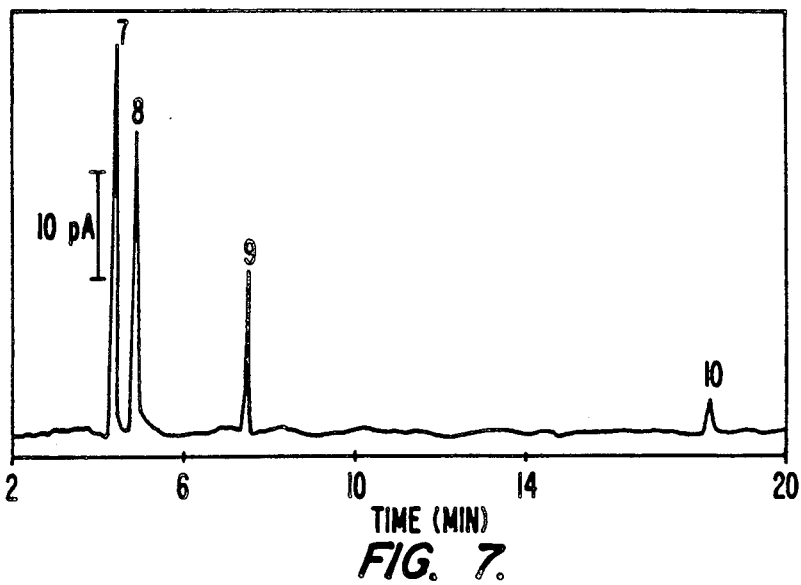
FIG. 7 is an electropherogram obtained with end-column amperometric detection.

The electropherogram in FIG. 7 shows the separation of equimolar ($1 \times 10^{-5}$M) concentrations of dopamine (peak 7), isoproterenol (peak 8), catechol (peak 9), and 3,4-dihydroxyphenylacetic acid (peak 10) obtained with a 5 μm i.d. capillary that was 56.6 cm long. It is clear that cations, neutrals, and anions are readily separated using this technique.

Figure 8:
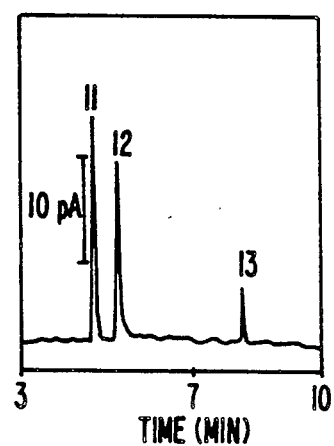
FIG. 8 is an electropherogram obtained with end-column amperometric detection.

FIG. 8 shows an electropherogram obtained in a separate study of the linearity of the detection system. An equimolar ($5 \times 10^{-6}$) mixture of dopamine (peak 11), isoproterenol (peak 12), and catechol (peak 13) was injected onto a 5 μm i.d., 56.6 cm long capillary. The peaks correspond to 960 amol dopamine, 870 amol isoproterenol, and 560 amol catechol. No attempt was made to optimize these separations.

Standard calibration curves for test solutes were computed. In one set of experiments, detection of catechol was examined for total injection amounts ranging from 1.13 fmol to 0.113 pmol ($10^{-5}$ to $10^{-3}$M). Linear regression analysis provided values for the slope, and correlation coefficient of $7.7 \times 10^{-3}$ and 0.991, respectively.

In another set of experiments, detection of dopamine, isoproterenol, and catechol was examined for average total injection amounts ranging from 80 amol to 4.0 fmol ($5.0 \times 10$ to $2.5 \times 10^{-5}$M). Linear regression analysis provided correlation coefficients of 0.998 for DA, 0.999 for IP, and 0.993 for CAT. The detection limits computed for these compounds are 64 amol for DA, 70 amol for IP, and 56 amol for CAT (S/N=2, peak-to-peak noise evaluated over 10 peak widths). These values were calculated based on the lowest amount injected, which was $5 \times 10^{-7}$M (80 amol).

It is to be understood that while the invention has been described above in conjunction with preferred specific embodiments, the description and examples are intended to illustrate and not limit the scope of the invention, which is defined by the scope of the appended claims.

What is claimed:

1. A capillary electrophoresis apparatus comprising:
    a separation capillary having an outlet end through which an electrophoretically separated component moves;
    a reservoir containing a buffer, the outlet end of the separation capillary being submerged in the buffer;
    a sensing electrode, positioned adjacent to and outside the outlet end of the separation capillary in the buffer, that responds to the component as it flows out of the separation capillary; and
    a reference electrode positioned in the buffer;
    means for passing a current between the electrodes; and
    means for measuring change in an electrical parameter between the two electrodes in response to the component.

2. An apparatus as defined in claim 1 wherein the distance between the sensing electrode and the outlet is sufficiently small so that as the component flows out of the separation capillary the component is not substantially diluted by buffer.

3. An apparatus as defined in claim 1 further comprising a second capillary into which the sensing electrode is inserted, wherein said second capillary is positioned adjacent to and outside the outlet end of the separation capillary to define an eluent gap through which the component flows.

4. The apparatus of claim 3, wherein the eluent gap is in the range of about 1 to 5 microns in dimensions.

5. The apparatus of claim 1, wherein the sensing electrode is placed at a distance in the range of about 1 to 5 microns from the outlet end.

6. An apparatus as defined in claim 1 further comprising means for establishing an eluent gap through which the component flows.

7. An apparatus as defined in claim 1 said reference electrode being a grounding electrode wherein said parameter is the electrical resistance or conductance of the component.

8. An apparatus as defined in claim 3, wherein said parameter is the current passing between the electrodes.

9. An apparatus as defined in claim 1 wherein the distance between the sensing electrode and the outlet end is sufficiently small so that as the component flows out of the separation capillary, the component comes in substantially continuous contact with the sensing electrode.

10. An apparatus as defined in claim 9, wherein the reference electrode and the sensing electrode form an electrode pair for detecting the electrochemical reactions at the sensing electrode.

11. An apparatus as defined in claim 1, wherein the reference electrode and the sensing electrode form an electrode pair for detecting the electrochemical reactions at the sensing electrode.

12. An electrical detection method useful in capillary electrophoresis comprising the steps of:
    positioning the outlet end of a separation capillary into a buffer reservoir;
    positioning a sensing electrode at a sufficiently small distance outside the outlet end of the separation capillary so that as a separated component flows out of the separation capillary, the component is not substantially diluted by the buffer;
    placing a grounding electrode in the buffer;
    establishing a current between the sensing electrode and grounding electrode;
    establishing an eluent gap through which the component flows; and
    measuring the change in electrical resistance or conductance between the electrodes.

13. The method of claim 11, further comprising applying an electrical potential between two points along the separation capillary, one point being the outlet end, for electrophoretic separation.

14. An electrochemical detection method useful in capillary electrophoresis comprising the steps of:
    positioning the outlet end of a separation capillary into a buffer reservoir;
    positioning a sensing electrode at a sufficiently small distance outside the outlet end so that as a separated component flows out of the separation capillary, the component comes in substantially continuous contact with the sensing electrode;
    placing a reference electrode in the buffer;
    applying a current between the sensing electrode and reference electrode; and
    measuring the change in current between the electrodes in response to the component.

15. The method of claim 14, further comprising applying an electrical potential between two points along the separation capillary, one point being the outlet end, for electrophoretic separation.

16. The apparatus of claim 1, further comprising means for applying electrical potential along the capillary between first and second points for causing electrophoretic separation, wherein the first point is at the outlet end.

17. The apparatus of claim 16, wherein said electrical potential applying means includes:
    a first electrode electrically coupled to the second point of the capillary; and
    a second electrode electrically coupled to the outlet end.

18. The apparatus of claim 17, wherein the second electrode is also the reference electrode, said reference electrode being substantially at ground potential with respect to the sensing electrode.

19. The apparatus of claim 17, wherein the second electrode is different from the reference electrode.

* * * * *

UNITED STATES PATENT AND TRADEMARK OFFICE
CERTIFICATE OF CORRECTION

PATENT NO.  : 5,126,023
DATED       : June 30, 1992
INVENTOR(S) : Xiaohua Huang, Richard N. Zare, Andrew G. Ewing, Sandra E. Sloss It is certified that error appears in the above-identified patent and that said Letters Patent is hereby corrected as shown below:

Column 8, line 29, in Claim 13        replace "claim 11" with ---claim 12---

Signed and Sealed this

Twenty-sixth Day of October, 1993

Attest:

BRUCE LEHMAN

Attesting Officer    Commissioner of Patents and Trademarks